(12) United States Patent
Propp

(10) Patent No.: US 8,053,623 B2
(45) Date of Patent: *Nov. 8, 2011

(54) REINFORCED CLOSURE ANCHOR

(75) Inventor: Donald J. Propp, Dewitt, MI (US)

(73) Assignee: Centurion Medical Products Corporation, Howell, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/690,315

(22) Filed: Jan. 20, 2010

(65) Prior Publication Data

US 2010/0121282 A1 May 13, 2010

Related U.S. Application Data

(63) Continuation-in-part of application No. 12/558,634, filed on Sep. 14, 2009, which is a continuation of application No. 12/011,692, filed on Jan. 29, 2008, now Pat. No. 7,626,070.

(51) Int. Cl.
*A61C 13/00* (2006.01)
*A61D 1/00* (2006.01)
*A61M 5/32* (2006.01)

(52) U.S. Cl. ............... 602/41; 606/213; 604/15

(58) Field of Classification Search .............. 602/41–43, 602/45, 52–54, 57–58; 606/213, 215, 139, 606/216, 228–232; 604/15, 180, 179, 174; 128/DIG. 26, 133, 132
See application file for complete search history.

(56) References Cited

U.S. PATENT DOCUMENTS

| | | | | |
|---|---|---|---|---|
| 5,553,605 | A * | 9/1996 | Muchin | 128/200.24 |
| 5,611,333 | A * | 3/1997 | Johnson | 128/200.24 |
| 6,124,521 | A * | 9/2000 | Roberts | 602/54 |
| 7,294,752 | B1 * | 11/2007 | Propp | 602/58 |
| 7,626,070 | B2 * | 12/2009 | Propp | 604/180 |
| 7,723,561 | B2 * | 5/2010 | Propp | 602/58 |
| 2005/0131329 | A1 | 6/2005 | Beaudry | |
| 2005/0261623 | A1 | 11/2005 | Propp | |
| 2007/0060892 | A1 | 3/2007 | Propp | |
| 2008/0200880 | A1 * | 8/2008 | Kyvik et al. | 604/180 |
| 2010/0004680 | A1 * | 1/2010 | Propp | 606/213 |
| 2010/0198162 | A1 * | 8/2010 | Propp | 604/180 |

* cited by examiner

*Primary Examiner* — Kim Lewis
*Assistant Examiner* — Tarla Patel
(74) *Attorney, Agent, or Firm* — Bill C. Panagos; Linda D. Kennedy; Rader, Fishman & Grauer PLLC

(57) ABSTRACT

A reinforced closure anchor includes a first layer having an adhesive side, an opposite non-adhesive side, and an outer edge. An anchor member layer having a reinforcing structure is disposed on the first layer. The anchor member includes an adhesive side and an opposite non-adhesive side. The anchor member adhesive side is adhered to the first layer non-adhesive side. The anchor member is disposed within the outer edge of the first layer.

20 Claims, 10 Drawing Sheets

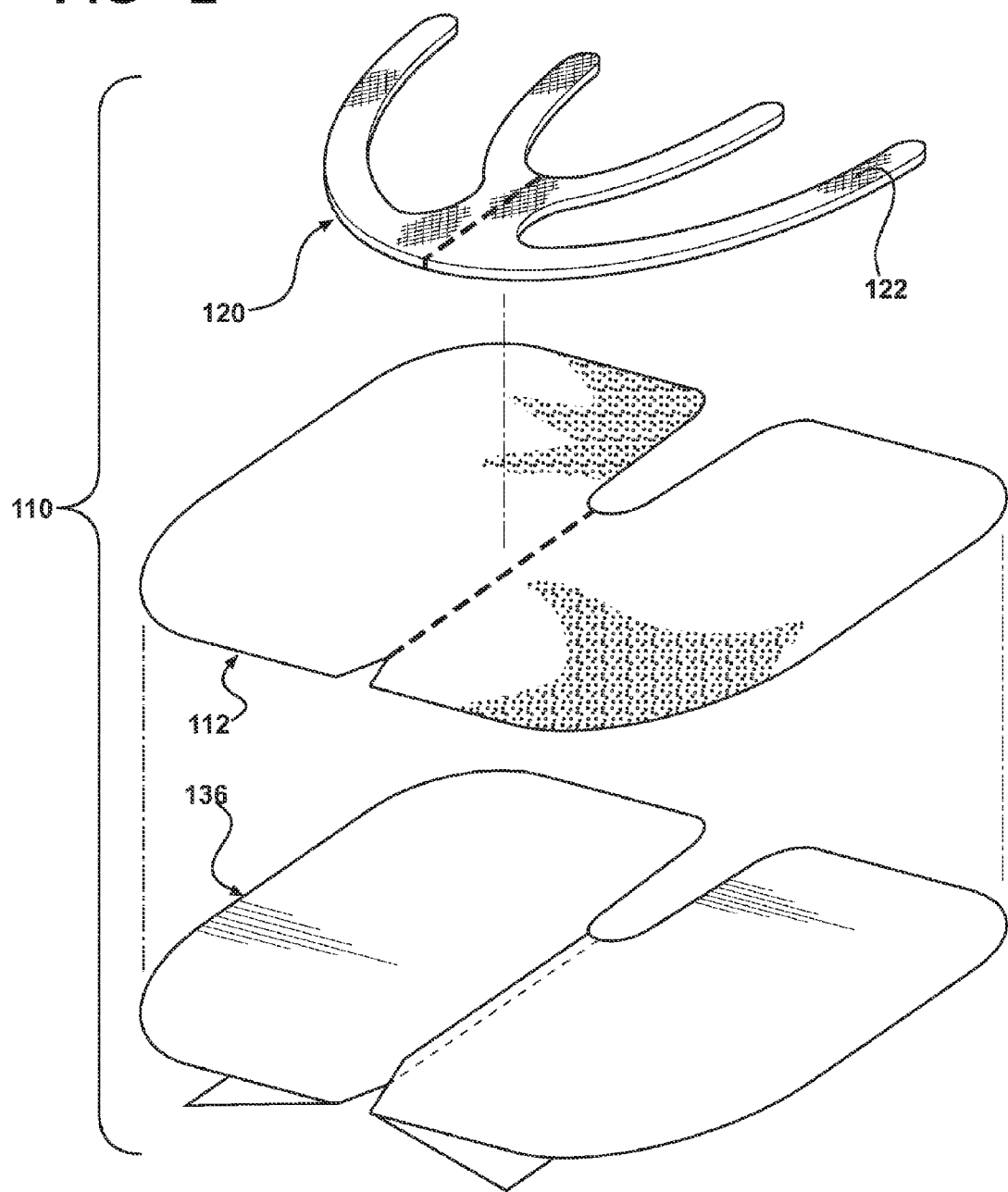

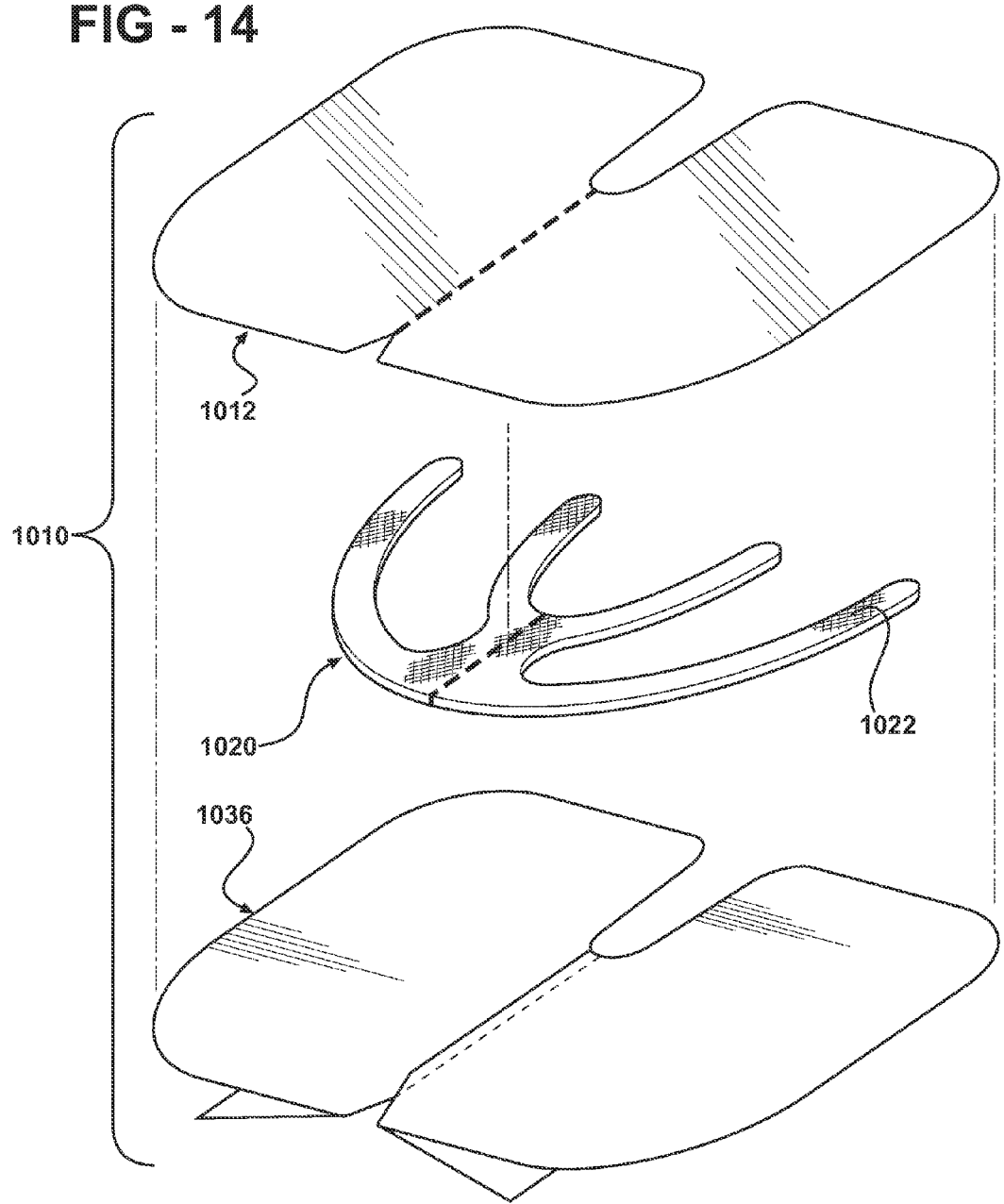

REINFORCED CLOSURE ANCHOR

CROSS REFERENCE TO RELATED APPLICATIONS

This application is a continuation-in-part of U.S. patent application Ser. No. 12/558,634, filed Sep. 14, 2009, which is a continuation of U.S. patent application Ser. No. 12/011,692, filed Jan. 29, 2008, now U.S. Pat. No. 7,626,070.

TECHNICAL FIELD

This invention relates to medical dressings, and more particularly to reinforced closure members for closing a portion of a medical dressing and anchoring medical tubing.

BACKGROUND OF THE INVENTION

It is known in the art relating to medical dressings for the protection and securement of catheters to apply a dressing to a patient's skin to cover a catheter insertion site at which the catheter punctures a patient's skin. It is also common for medical clinicians (i.e., doctors, nurses, and other medical personnel) to alternatively or additionally apply strips of medical grade tape to attempt to secure the catheter or associated medical tubing. Another conventional clinical practice is to suture a catheter hub to a patient's skin to invasively and roughly secure the catheter to the patient. Further still, a variety of catheter and medical tubing securement devices are available for use in the medical field. These securement devices, however, are often bulky and cumbersome, hard to dress and/or remove with a dressing, may require a scissors or scalpel to physically cut them away risking catheter lumen or catheter pigtails damage in the process, may require two, three, or four pieces of tape to get reliable results, and may have costly and complex mechanical features; all of which can combine to both lower patient care clinical outcomes, and equally important, lead to higher healthcare costs due to added nursing costs.

It is also known in the medical field that poorly dressed and poorly secured catheters and associated tubing are likely to undesirably lead to irritation of both internal vascular wall damage at distal catheter tip due to in/out catheter tip motion at the insertion site, necessitating premature rotation and reinsertion of the catheter to a nearby new anatomical insertion site. Even worse, poorly secured catheters are susceptible to accidental dislodgement from the insertion site. For example, medical tubing connected to indwelling catheters, infusion needles and the like is often subjected to inadvertent but significant pulling forces either caused directly by patient movement or by snagging of the tubing on other objects. These pulling forces peel the medical tape or dressing securing the catheter and/or tubing off the patient's skin. This exposes the catheter, infusion needle, etc. to movement inward or outward, increasing the likelihood that the catheter, infusion needle, etc. will fail and have to be replaced and inserted into a new insertion site. Also, this may weaken the adhesion between the dressing and the patient's skin, potentially exposing the insertion site to harmful bacteria.

SUMMARY OF THE INVENTION

The present invention provides a reinforced closure anchor that can close over and anchor a slit, perforation, notch, or edge portion of a medical dressing at which a catheter and/or tubing exits from underneath the dressing. The reinforced closure anchor helps prevent a dressing from inadvertently peeling from a patient's skin, which may be caused by tugging on tubing that is under and exiting from the dressing, by both covering over a portion of the medical dressing and by securing an area of the dressing at which medical tubing exits from underneath the dressing. The reinforced closure anchor also prevents inadvertent peeling by providing additional material beyond the dressing edge, thereby greatly multiplying the dressing withstand in tug force vector directions opposite to (and at any relative angle to, over an entire hemispherical (half globe) field of tug force vectors) that which tubing exits from the dressing. Also, the reinforced closure anchor limits the amount of fabric cloth stretching that can occur by using relatively non-elastic reinforcement material for a spinal structure, which limits the amount and size of a "hole" that can be stretched open by tugs, and thus prevents catheter hubs and/or tubing from "oozing" out of a dressing. And due to the narrow spinal structure's limited portion of entire closure's surface area, higher moisture vapor transmission rate is possible over as much as 90 to 95 percent of the closure's total skin contacting and dressing overlapping surface area.

More particularly, a reinforced closure anchor in accordance with the invention includes a first layer having an adhesive side, an opposite non-adhesive side, and an outer edge. An anchor member layer having a reinforcing structure, an adhesive side, and an opposite non-adhesive side is disposed on the "top" of the first layer. The anchor member adhesive side is adhered to the first layer non-adhesive side. The anchor member may be disposed within the outer edge of the first layer, although it is within the scope of the invention for the anchor member to be coincident with the outer edge. The anchor member may be one of a generally fork shape, a spine and rib shape, a narrow fingers shape, a sinuous shape, a linear shape, an H-like shape, a W-like shape, and a discontinuous array of spacedly disposed islands shape.

The first layer may be a fabric layer and may additionally include a film layer having an adhesive skin-adhering side and an opposite side adhered to the first layer adhesive side. Alternatively, the first layer may be a film layer.

The anchor member may be smaller in surface area than the first layer. For example, the anchor member may have less than half the surface area of the first layer. Also, the anchor member may cover only a portion of the first layer non-adhesive side.

The reinforced closure anchor may be generally symmetrical about one of its axes. A perforation line may extend across the first layer and the anchor member. The perforation line may extend along the axis of symmetry. A V-shaped notch may be disposed along the outer edge of the first layer at an end of the perforation line. A U-shaped indentation also may be disposed along the outer edge of the first layer.

The reinforced closure anchor may include a release liner releasably mounted on the adhesive side of the first (or "bottom") layer. The release liner may include a first member and a second member. Each of the first member and second member may include a first portion mounted on the adhesive side of the first layer and a second portion folded relative to the first portion to form a gripping tab. One of the first and second members may overlap the other of the first and second members, and one of the first and second members may be released from the adhesive side of the first layer without tampering with the other of the members.

In another embodiment, a reinforced closure anchor in accordance with the invention includes a film layer having an adhesive side, an opposite non-adhesive side, and an outer edge. An anchor member layer having a reinforcing structure, a first side, and an opposite second side is disposed adjacent the film layer. The anchor member second side is adhered to the film layer adhesive side. The anchor member is disposed within the outer edge of the film layer.

Optionally, the anchor member first side may include an adhesive thereon, or the anchor member first side may be free of adhesive. The anchor member may be smaller in surface area than the film layer.

These and other features and advantages of the invention will be more fully understood from the following detailed description of the invention taken together with the accompanying drawings.

BRIEF DESCRIPTION OF THE DRAWINGS

In the drawings:

FIG. 2 is an exploded view of the reinforced closure anchor of FIG. 1;

FIG. 14 is an exploded view of the reinforced closure anchor of FIG. 13; and

DETAILED DESCRIPTION OF THE INVENTION

Figure 1:
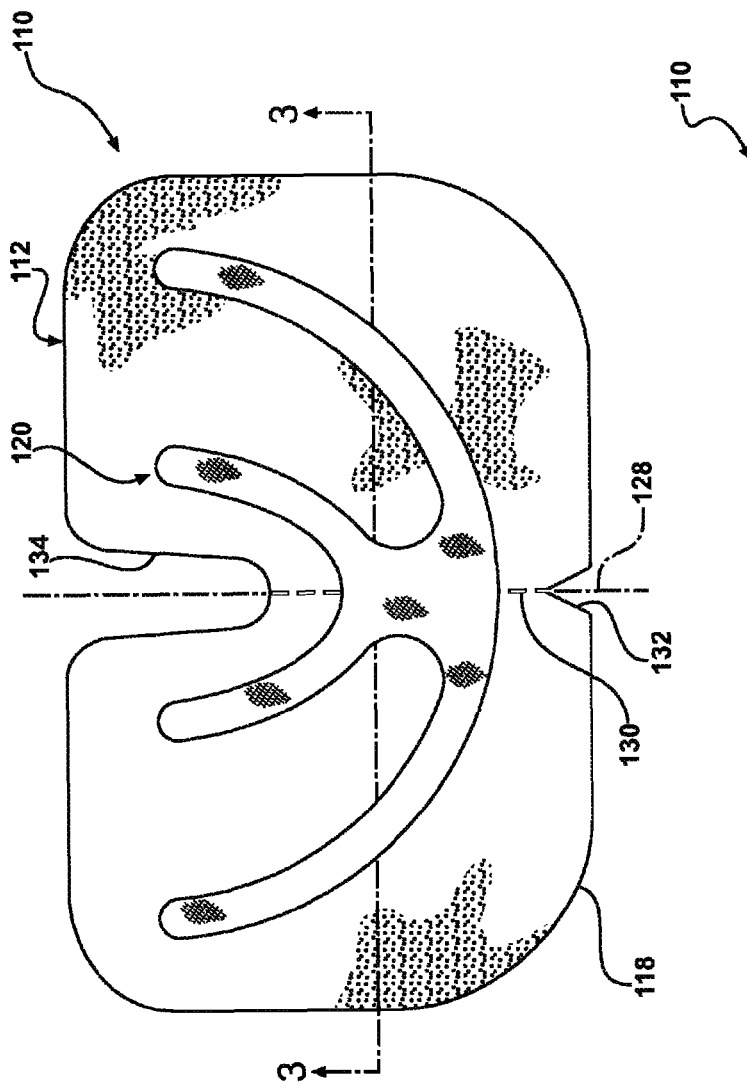
FIG. 1 is a plan view of one embodiment of a reinforced closure anchor in accordance with the invention.

Referring now to the drawings in detail, numeral 110 generally indicates a reinforced closure anchor in accordance with the invention. The reinforced closure anchor 110 may secure a portion of a medical dressing, such as a portion at which medical tubing exits from underneath the dressing. The reinforced closure anchor 110 counteracts tugging forces from any hemispherical vector direction that may be applied on the medical tubing and helps prevent the tugging forces from pulling the dressing away from a patient's skin.

Figure 3:
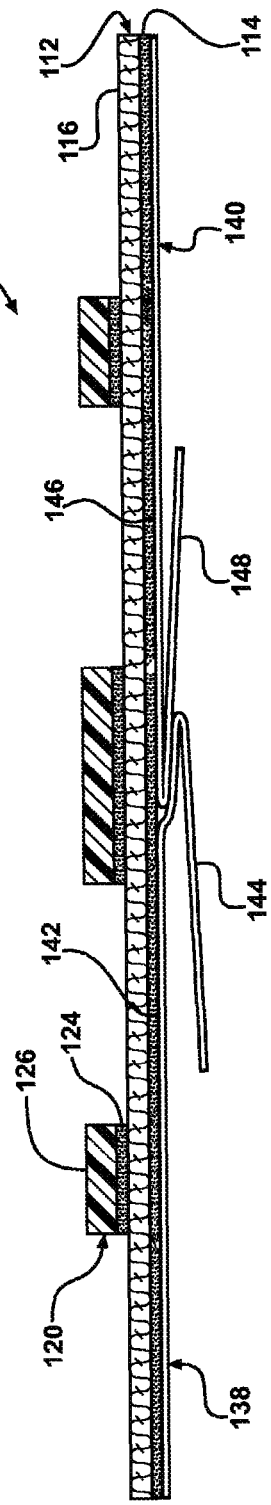
FIG. 3 is a cross-sectional view of the reinforced closure anchor taken along the line 3-3 in FIG. 1.

Turning to FIGS. 1 through 3, the reinforced closure anchor 110 includes a first layer 112 having an adhesive side 114 including an adhesive such as a medical skin contact grade adhesive or similarly suitable adhesive thereon. The first layer 112 also has an opposite non-adhesive side 116 and an outer edge 118. The first layer 112 is not limited to any particular shape. In the embodiment shown in the drawings, the first layer 112 is generally rectangular in shape with curved corners. The first layer 112 may be made of a woven or non-woven fabric material. Alternatively, the first layer 112 may be made of a film such as a polyurethane film or similar.

An anchor member layer 120 including a reinforcing structure 122 is disposed on a "top" side of the first layer 112. The anchor member 120 may be made of a polypropylene or polyethylene net or net-like material or another similar material, such as woven or non-woven or cellulosic or foam or other laminar materials having sufficient non-elastic properties yet being flexible, "contourable" and permeable, and having rigidizing and force spreading properties as discussed below, wherein the netting defines the reinforcing structure 122. The anchor member 120 has an adhesive side 124 including a suitable adhesive thereon. The anchor member 120 also has an opposite non-adhesive side 126. The anchor member adhesive side 124 is adhered to the first layer non-adhesive side 116. The anchor member 120 is disposed within the outer edge 118 of the first layer 112.

Figure 4:
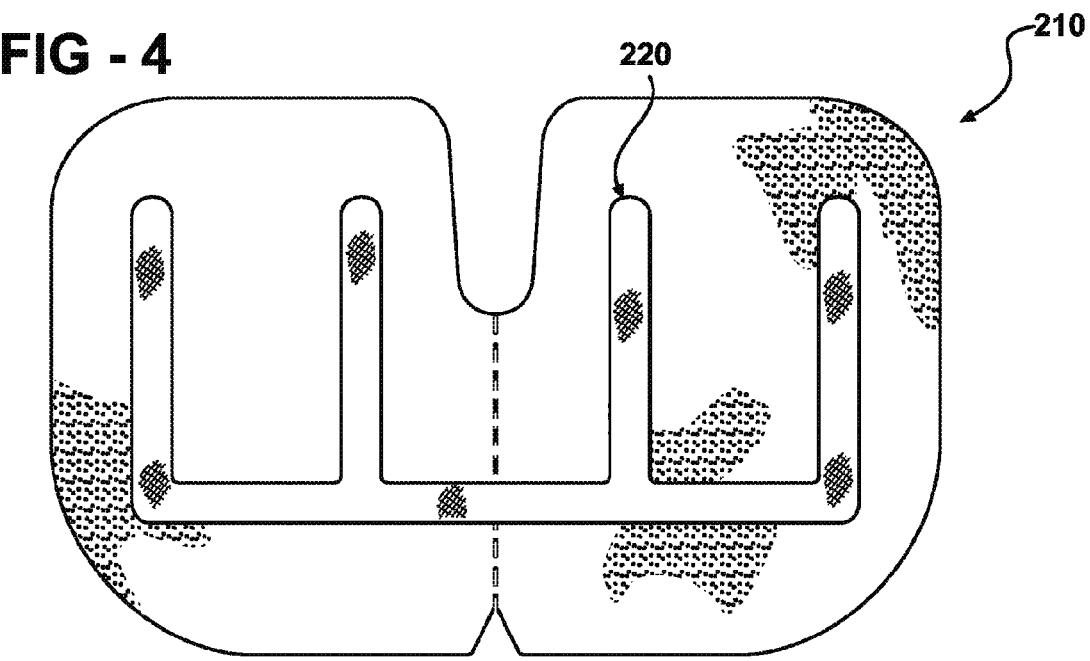
FIG. 4 is a plan view of a reinforced closure anchor in accordance with the invention.
Figure 5:
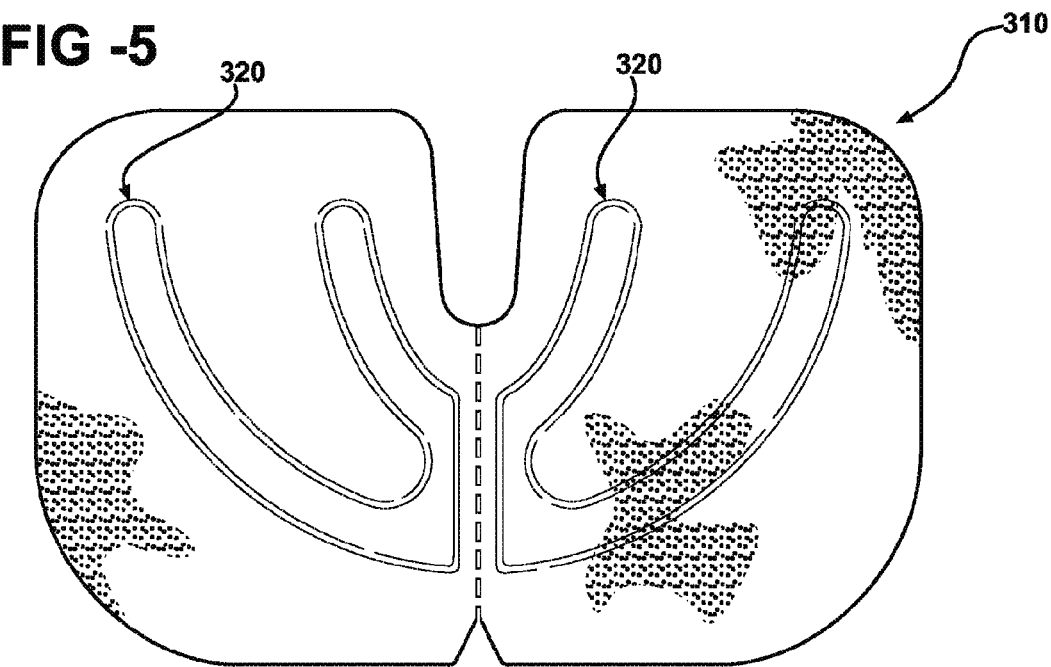
FIG. 5 is a plan view of a reinforced closure anchor in accordance with the invention.
Figure 6:
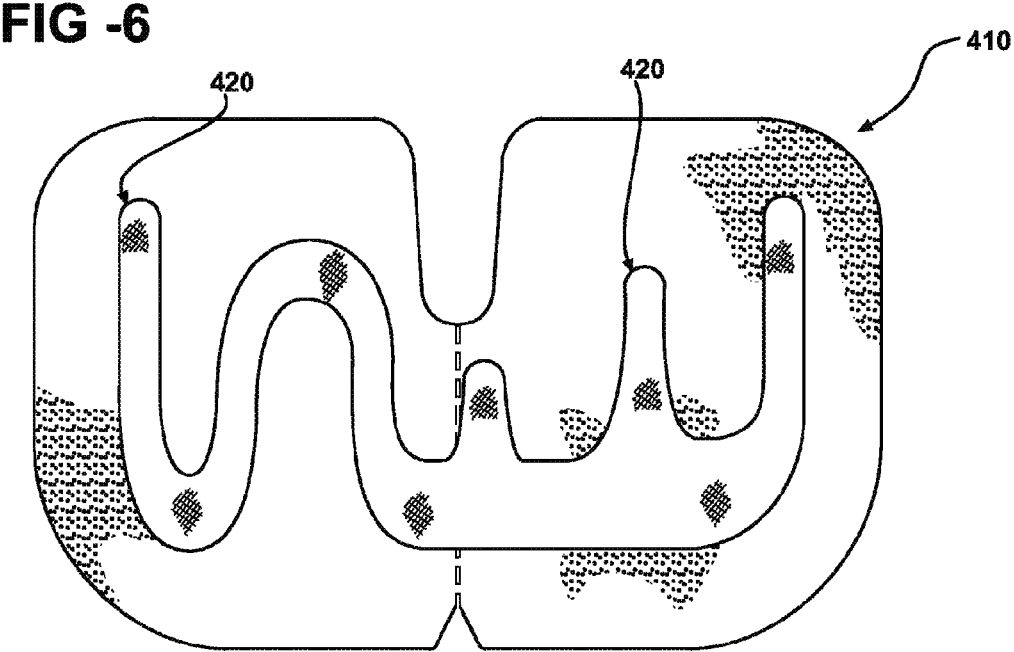
FIG. 6 is a plan view of a reinforced closure anchor in accordance with the invention.
Figure 7:
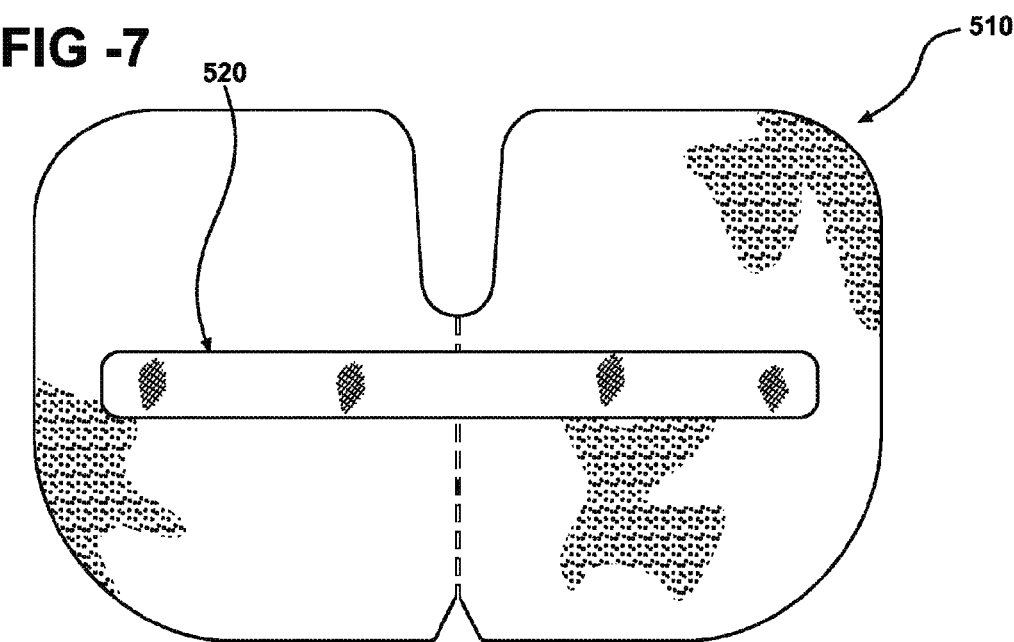
FIG. 7 is a plan view of a reinforced closure anchor in accordance with the invention.
Figure 8:
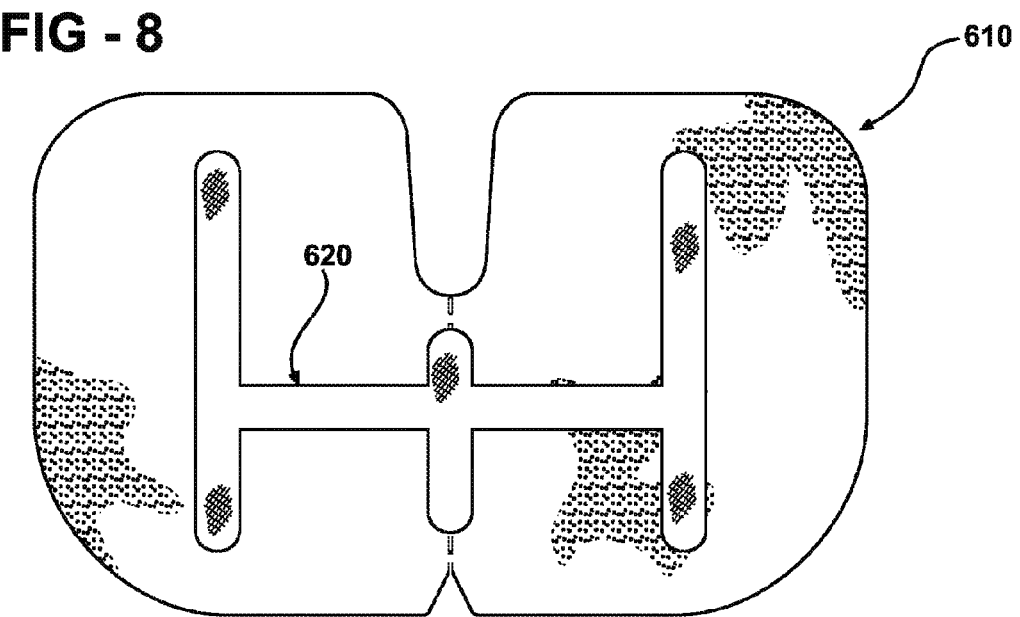
FIG. 8 is a plan view of a reinforced closure anchor in accordance with the invention.
Figure 9:
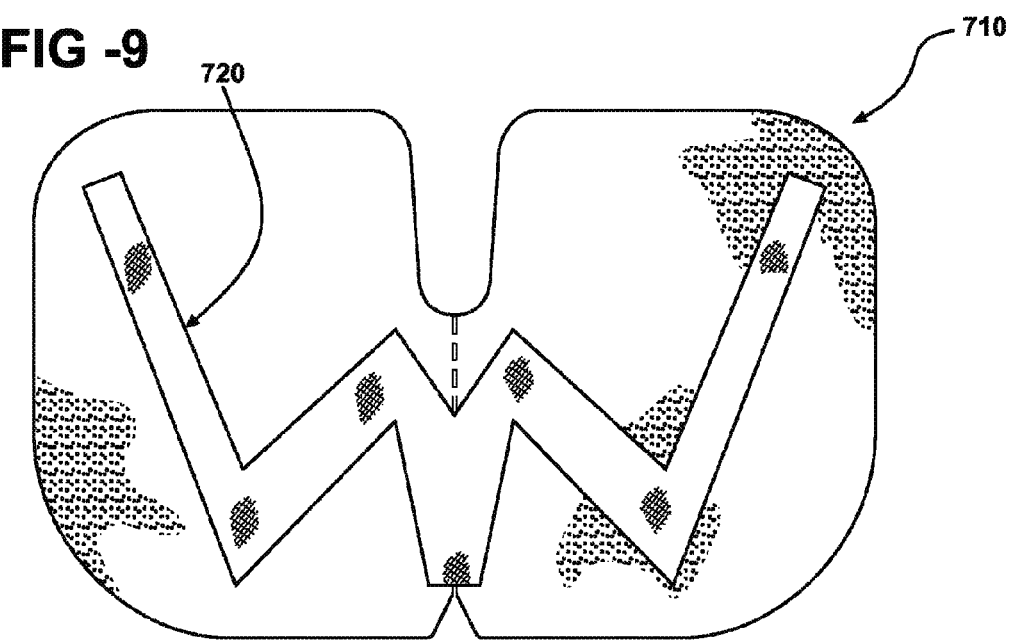
FIG. 9 is a plan view of a reinforced closure anchor in accordance with the invention.
Figure 10:
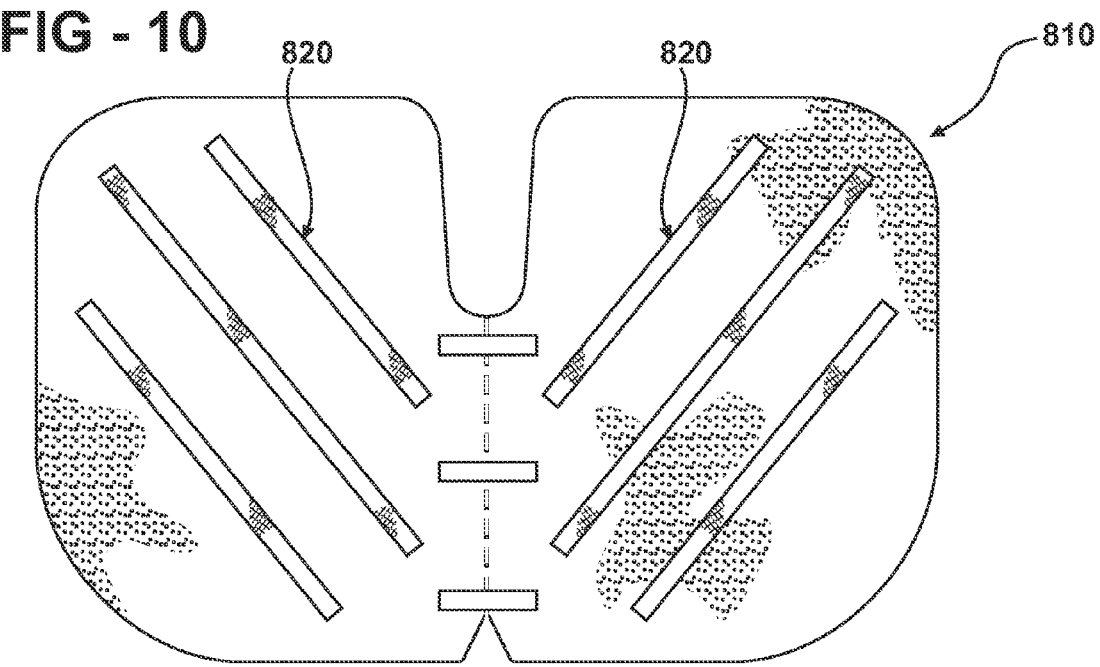
FIG. 10 is a plan view of a reinforced closure anchor in accordance with the invention.

The anchor member 120 is not limited to any particular shape, although the anchor member typically has less surface area than the first layer such that the anchor member only overlaps a portion of the first layer. For example, the anchor member 120 may have less than half the surface area of the first layer 112. In a first embodiment 110 shown in FIGS. 1-3, the anchor member 120 has a generally fork shape. In a second embodiment 210 shown in FIG. 4, the anchor member 220 generally has a spinal rib shape that fits around and behind exiting catheter lumen, hubs, or IV tubing. The shape of the anchor member 220 ensures contourability to patient body curvatures, and minimally reduces the breathability of the closure anchor, and of the dressing laminates stack-up and closure anchor laminates stack-up combination. The anchor member may have more or less than four tines and/or may be wider or narrowly spaced between the tines. Also, the anchor member may be very narrowly spaced between innermost tines, to create a "keyhole"-like effect at the dressing exit and the anchor member's innermost bottom of the U-shape, from which it is very difficult for a catheter hub to ever slide out of when the closure anchor is cinched up tightly to exiting tubing. In a third embodiment 310 shown in FIG. 5, the anchor member 320 has a narrow fingers shape to ensure contourability to patient body curvatures, and to minimally reduce the breathability of the closure anchor, and of the dressing stack and closure anchor stack combination. In a fourth embodiment 410 shown in FIG. 6, the anchor member 420 has a generally sinuous shape. In a fifth embodiment 510 shown in FIG. 7, the anchor member 520 has a generally linear shape. In a sixth embodiment 610 shown in FIG. 8, the anchor member 620 has a generally H-shape. In a seventh embodiment 710 shown in FIG. 9, the anchor member 720 shown in FIG. 9, the anchor member 720 has a generally W-shape. In an eighth embodiment 810 shown in FIG. 10, the anchor member 820 is a discontinuous array of island portions.

Figure 11:
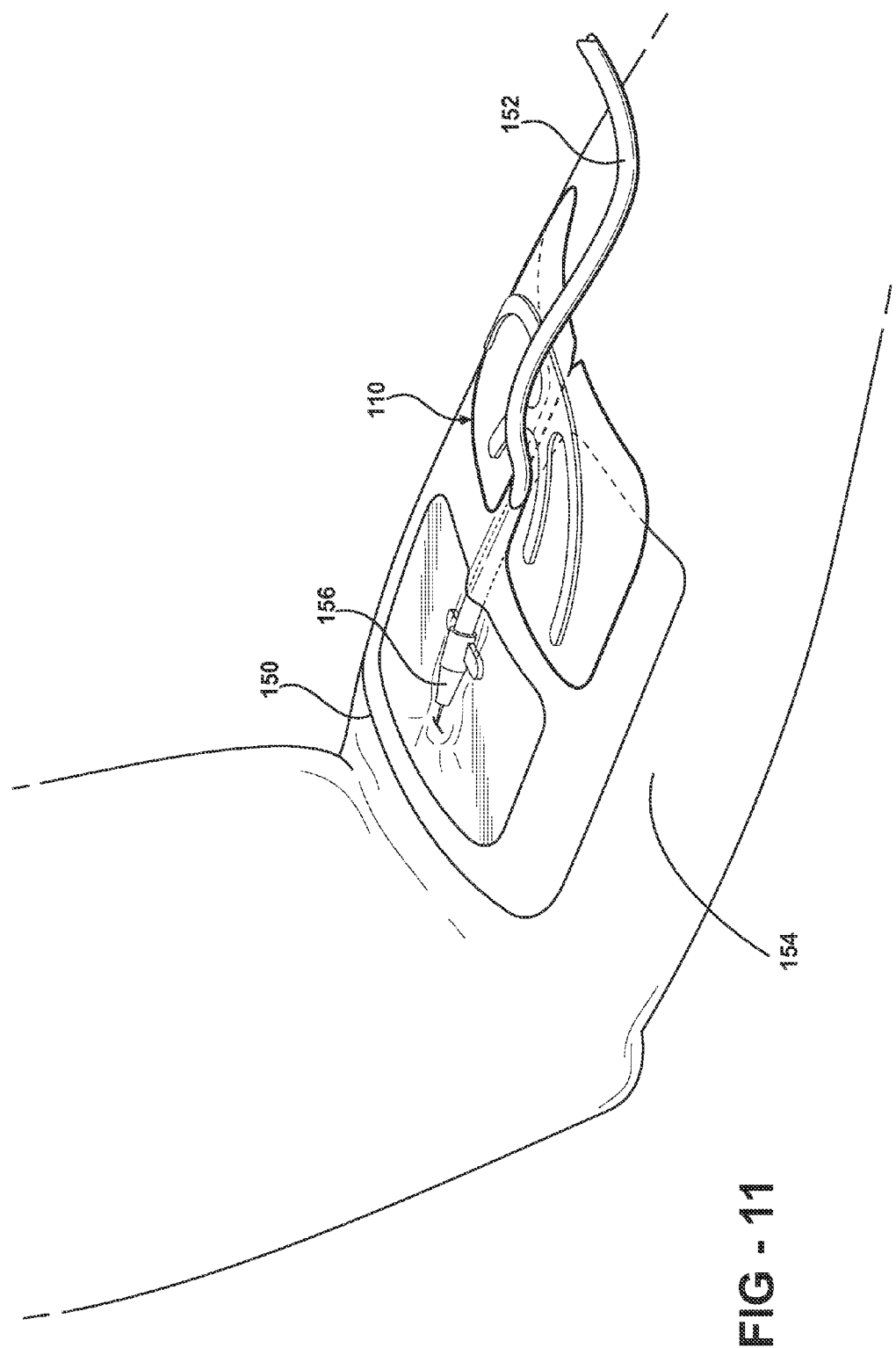
FIG. 11 is an environmental view of the reinforced closure anchor of FIG. 1 securing and stabilizing a dressing.

The anchor member 120 strengthens the reinforced closure anchor 110 by making it less floppy for easier application. More importantly, as shown in FIG. 11, when the reinforced closure anchor 110 is applied over a portion of a dressing 150 and under the exiting tubing 152 (as well as to a patient's skin 154 where it is not over the dressing), the anchor member 120 spreads the localized external tubing tug forces that are exerted on the dressing 150 and the reinforced closure anchor 110 over a large surface area, greatly increasing the dressing's resistance to premature separation from the patient's skin by not permitting the dressing to elongate and break the adhesive forces between the dressing and the patient's skin. Likewise, the anchor member 120 increases the amount of force necessary to separate the dressing 150, and thus the catheter 156, from a patient's skin 154. With the use of the reinforced closure anchor 110, external forces exerted on a dressing are not as localized. Highly concentrated localized tug forces are a typical reason small forces are able to commence peeling of a dressing by stretching the fabric and film of the dressing in a local area which then propagates onward. Commonly, forces external to the dressing are exerted on a dressing by pulling, snagging, or tugging on the IV connector ports, IV valves, pigtails, lumen, fittings, and/or medical fluid administration tubing that are connected to a catheter underneath the dressing. For example, movement of the medical tubing may be caused by the patient moving, by snagging of the tubing on other neighboring objects, by a clinician moving the tubing or the patient, or any combination of the above. The reinforced closure anchor 110 also prevents premature separation of a dressing from a patient's skin by preventing the dressing from stretching and thus peeling when the dressing is tugged on as described above, for example, when the tubing connected to the catheter hub is pulled. Stretching of a dressing locally (and resultant peel propagation) can ultimately lead to a dressing separating fully from a patient's skin. In sum, the reinforced closure anchor 110 greatly increases the withstand of a dressing and greatly increases the amount of any hemispherical vector multi-directional pulling force that is necessary to cause a dressing to separate from a patient's skin. This leads directly to longer dwell times, better patient care, lower nursing time, and lower healthcare costs.

The reinforced closure anchor 110 may be generally symmetrical about one of its axes 128. A closure perforation line 130, for easy removal of the closure anchor and associated dressing, may extend across the first layer 112 and the anchor member 120. In other words, the reinforced closure anchor 110 is perforated through all of layers (not including any release liner layer(s)—see below) along the perforation line 130. The perforation line 130 may extend along the axis of symmetry 128, thereby dividing the reinforced closure anchor 110 into two mirror image portions and allowing the reinforced closure anchor to be separated at a dressing removal time while the closure anchor is still overlapped onto the dressing on either side of the tubing. A V-shaped notch 132 may be disposed along the first layer outer edge 118 at an end of the perforation line 130. The V-shaped notch 132 serves as a landmark indicating where the perforation line 130 is located. A deep U-shaped recess 134 is disposed along the first layer outer edge 18. The U-shaped recess 134 may be at an opposite end of the perforation line 130 relative to the V-shaped notch 132. When the reinforced closure member 110 is applied to a dressing in an area where medical tubing exits from underneath the dressing, closure anchor's U-shaped recess 134 is slid under the tubing and overlapped on top of the dressing behind the catheter hub, creating opposing U-slot "keyholes" that the catheter hub cannot be easily tugged out of. The U-slot "keyholes" and the added surface area beyond the dressing's edge strengthen the dressing and greatly increase the magnitude of a tug force necessary to raise the dressing's edge from a patient's skin, thereby improving securement and stabilization. The U-shaped recess 134 also makes it easier to create an occlusive barrier at the tubing exit point.

The reinforced closure anchor may further include a release liner 136 releasably mounted on the adhesive side 114 of the first layer 112. The release liner 136 may include a first member 138 and a second member 140. The first member 138 includes a first portion 142 and a second portion 144 and the second member 140 includes a first portion 146 and a second portion 148. The first portions 142, 146 are mounted on the first layer adhesive side 114 and the second portions 144, 148 are folded relative to the first portions to form gripping tabs. The first member 138 may overlap the second member 140, and each of the first and second members may be released from the first layer adhesive side 114 without tampering with the other of the members.

To apply the reinforced closure anchor 110, preferably only one of the first and second members 138, 140 of the release liner 136 is removed to expose part of the first layer adhesive side 114. For example, the first member 138 may be removed by gripping the gripping tab 144 and pulling the first member 138 away from the fabric layer adhesive side 114. By leaving the second member 140 of the release liner 136 in place, a user may grasp part of the reinforced closure anchor 110 without the user's fingers becoming stuck to the reinforced closure anchor. Next, the reinforced closure anchor 110 is positioned where it is desired to apply the reinforced closure anchor 110. For example, the reinforced closure anchor 110 may be applied to an edge portion of a dressing at which tubing exits from underneath the dressing. The reinforced closure anchor 110 is positioned so that the closure anchor is under the tubing with the U-shaped recess 134 laying on either side of the tubing and overlapping the top surface of the dressing. The exposed first layer adhesive side 114 is then adhered to the outside of the dressing and any portion of the patient's skin that is exposed underneath the reinforced closure anchor. Next, the second member 140 of the release liner 136 is removed by pulling the gripping tab 148, and the rest of the reinforced closure anchor 110 is applied to the dressing and/or patient's skin.

Alternatively, the reinforced closure anchor 110 may be used in lieu of tape strips to secure medical tubing, such as IV tubing, to a patient's skin.

To remove the closure anchor 110 and dressing from a patient's skin, the closure anchor is separated along the perforation line 130 by tearing the perforation line. The closure anchor 110 and dressing may then be removed from the patient's skin as a single unit by pulling the closure anchor 110 and dressing away from the tubing and catheter hub, making it safer and easier to remove the dressing from the tubing and hub with a lowered risk of unwanted catheter movement.

Figure 12:
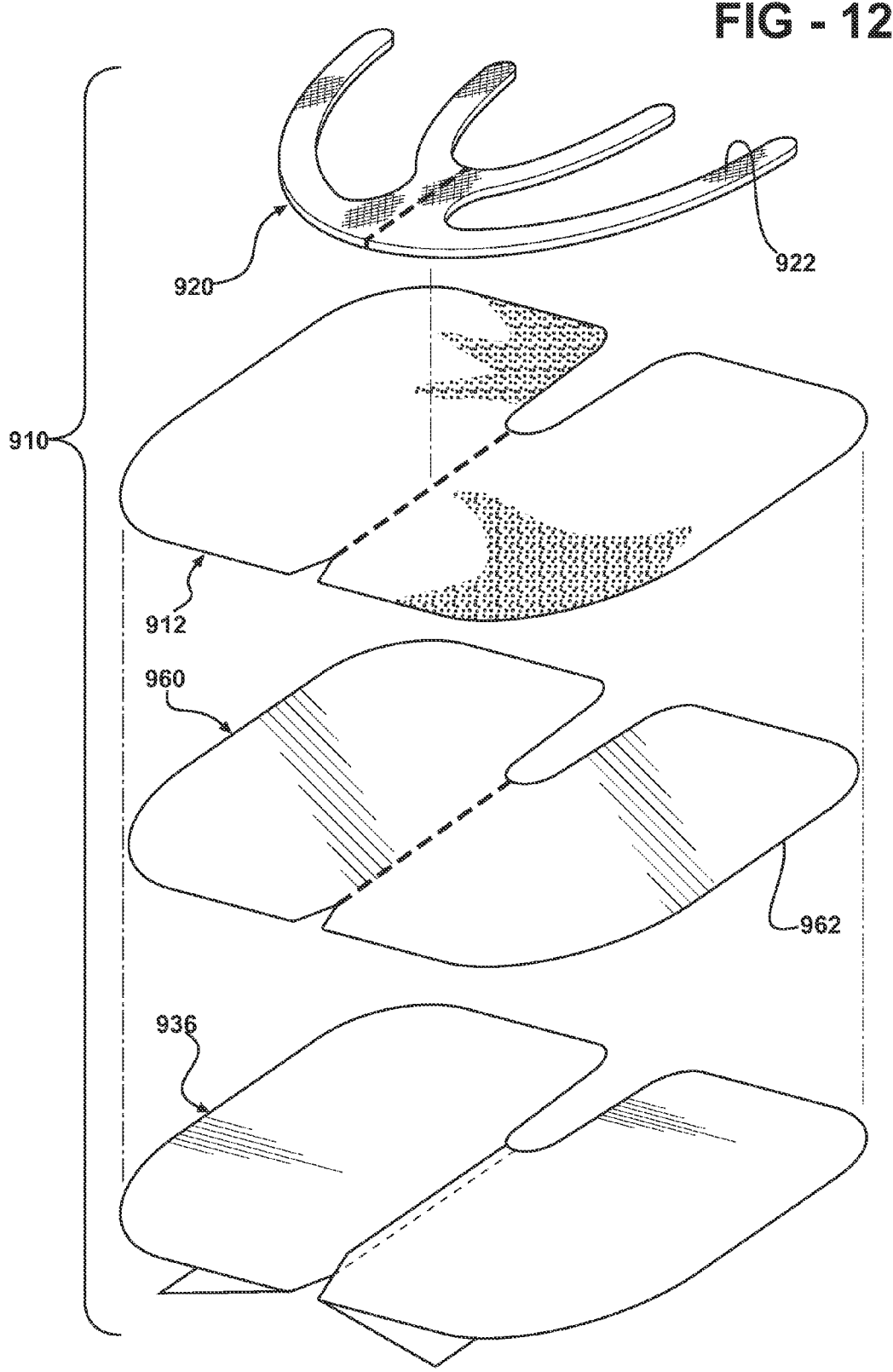
FIG. 12 is an exploded view of a reinforced closure anchor in accordance with the invention.

In an alternative embodiment, the reinforced closure anchor may further include both a fabric layer such as a woven or non-woven fabric or similar, and a film layer such as a polyurethane film or similar. As shown in FIG. 12, the reinforced closure anchor 910 includes a fabric layer 912 and an anchor member layer 920 including a reinforcing structure 922 disposed on and adhered to a "top", non-adhesive side of the fabric layer 912. The fabric layer 912 and anchor member layer 920 may have any of the features described in the previous embodiments. The reinforced closure anchor 910 further includes a film layer 960 having an adhesive skin-adhering side 962. The adhesive on the skin-adhering side 962 may be a medical skin contact grade adhesive or similarly suitable adhesive. A side of the film layer 960 opposite the skin-adhering side 962 is disposed adjacent the fabric layer 912 and is adhered to the fabric layer. A release liner 936 may be releasably mounted on the skin-adhering side 962 of the film layer 960. The film layer 960 may have a shape that is coincident with the fabric layer 912 and/or film layer 960. The film layer 960 may make the reinforced closure anchor 110 more comfortable for a patient by shielding the fabric layer 912 from the patient's skin. The film layer 960 also can create a bacterial barrier and can add stack strength to the closure anchor.

Figure 13:
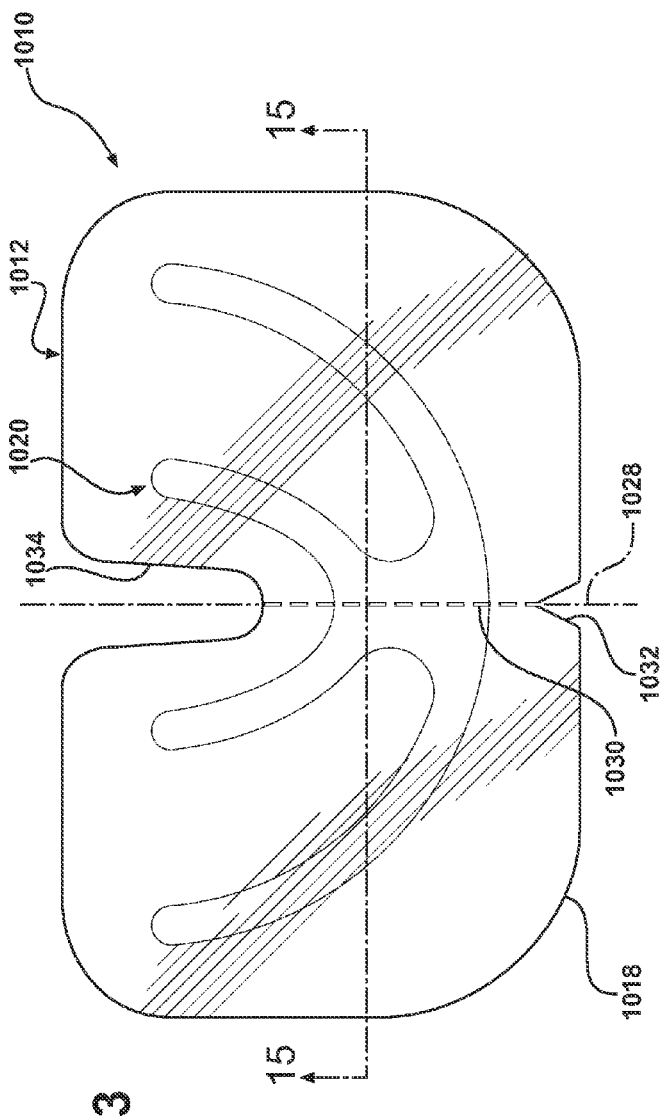
FIG. 13 is a plan view of a reinforced closure anchor in accordance with the invention.
Figure 15:
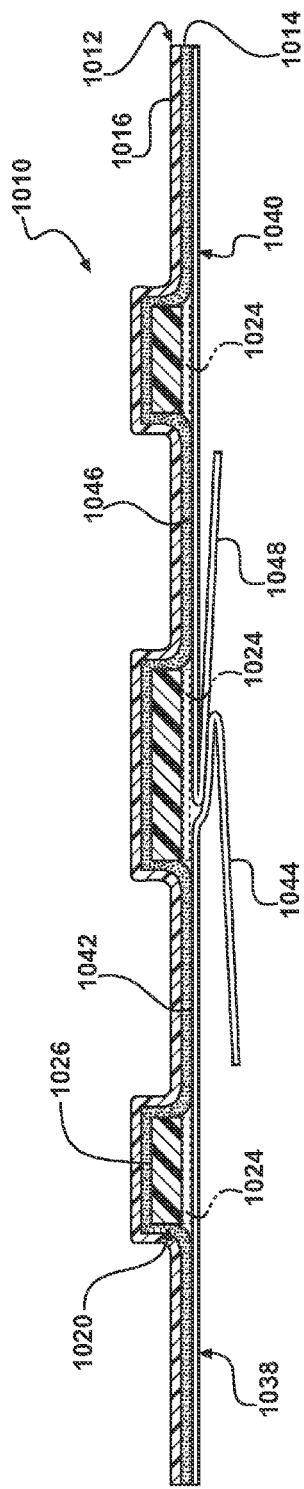
FIG. 15 is a cross-sectional view of the reinforced closure anchor taken along the line 15-15 in FIG. 13.

In yet another alternative embodiment shown in FIGS. 13-15, a reinforced closure anchor 1010 in accordance with the invention includes a first layer that is a film layer 1012 having an adhesive side 1014 including a medical skin contact grade adhesive or similarly suitable adhesive thereon. The film layer 1012 also has an opposite non-adhesive side 1016 and an outer edge 1018. The film layer 1012 may be a polyurethane film material or similar. The film layer 1012 is not limited to any particular shape. In the embodiment shown in the drawings, the film layer 1012 is generally rectangular in shape with curved corners.

An anchor member layer 1020 including a reinforcing structure 1022 is disposed adjacent the film layer 1012 and is disposed within the outer edge 1018 of the film layer 1012. The anchor member 1020 is similar in structure to the anchor member 20 and may have any of the properties of the anchor member 20 described above. The anchor member 1020 also may have any of the shapes of the anchor member 20, and is not particularly limited to one specific shape. The anchor member 1020 has a first side 1024 and an opposite second side 1026. Optionally, the first side 1024 may include a medical skin contact grade adhesive or similarly suitable adhesive thereon, or alternatively may include no adhesive. In contrast to the first embodiment 10, the anchor member second side 1026 is adhered to the film layer adhesive side 1014, i.e. the "bottom" side of the film layer 1012. Otherwise, the reinforced closure anchor 1010 has similar features and functions as the first embodiment 10.

For example, the reinforced closure anchor 1010 may be generally symmetrical about one of its axes 1028. A closure perforation line 1030, for easy removal of the closure anchor and associated dressing, may extend across the film layer 1012 and the anchor member 1020. In other words, the reinforced closure anchor 1010 is perforated through all of layers (not including any release liner layer(s)—see below) along the perforation line 1030. The perforation line 1030 may extend along the axis of symmetry 1028, thereby dividing the reinforced closure anchor 1010 into two mirror image portions and allowing the reinforced closure anchor to be separated at a dressing removal time while the closure anchor is still overlapped onto the dressing on either side of the tubing. A V-shaped notch 1032 may be disposed along the film layer outer edge 1018 at an end of the perforation line 1030. The V-shaped notch 1032 serves as a landmark indicating where the perforation line 1030 is located. A deep U-shaped recess 1034 is disposed along the film layer outer edge 1018. The U-shaped recess 1034 may be at an opposite end of the perforation line 1030 relative to the V-shaped notch 1032.

The reinforced closure anchor 1010 may further include a release liner 1036 releasably mounted on the adhesive side 1014 of the film layer 1012. The release liner 1036 may include a first member 1038 and a second member 1040. The first member 1038 includes a first portion 1042 and a second portion 1044 and the second member 1040 includes a first portion 1046 and a second portion 1048. The first portions 1042, 1046 are mounted on the film layer adhesive side 1014 and the second portions 1044, 1048 are folded relative to the first portions to form gripping tabs. The first member 1038 may overlap the second member 1040, and each of the first and second members may be released from the film layer adhesive side 1014 without tampering with the other of the members.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A reinforced closure anchor comprising:
    a first layer having an adhesive side, an opposite non-adhesive side, and an outer edge; and
    an anchor member layer having a reinforcing structure, an adhesive side, and an opposite non-adhesive side, said anchor member adhesive side being adhered to said first layer non-adhesive side;
    said anchor member being disposed within the outer edge of said first layer, and said anchor member being one of a generally fork shape, a spine and rib shape, a narrow fingers shape, a sinuous shape, a linear shape, an H-like shape, a W-like shape, and a discontinuous array of spacedly disposed islands shape.

2. The reinforced closure anchor of claim 1, wherein said first layer is a fabric layer.

3. The reinforced closure anchor of claim 2, including a film layer having an adhesive skin-adhering side and an opposite side adhered to said fabric layer adhesive side.

4. The reinforced closure anchor of claim 1, wherein said first layer is a film layer.

5. The reinforced closure anchor of claim 1, wherein said anchor member is smaller in surface area than said first layer.

6. The reinforced closure anchor of claim 5, wherein said anchor member has less than half the surface area of said first layer.

7. The reinforced closure anchor of claim 1, wherein said anchor member covers only a portion of said first layer non-adhesive side.

8. The reinforced closure anchor of claim 1, wherein said reinforced closure anchor is generally symmetrical about one of its axes.

9. The reinforced closure anchor of claim 1, including a perforation line extending across said first layer and said anchor member.

10. The reinforced closure anchor of claim 9, wherein said reinforced closure anchor is generally symmetrical about one axis, and said perforation line extends along said axis.

11. The reinforced closure anchor of claim 10, including a V-shaped notch along the outer edge of said first layer at an end of said perforation line.

12. The reinforced closure anchor of claim 1, including a U-shaped recess along the outer edge of said first layer.

13. The reinforced closure anchor of claim 1, including a release liner releasably mounted on the adhesive side of said first layer.

14. The reinforced closure anchor of claim 13, wherein said release liner includes a first member and a second member, each of the first member and second member including a first portion mounted on said adhesive side of said first layer and a second portion folded relative to said first portion to form a gripping tab;
    wherein one of said first and second members overlaps the other of said first and second members, and one of said first and second members is releasable from said adhesive side of said first layer without tampering with the other of said members.

15. The reinforced closure anchor of claim 3, including a release liner releasably mounted on the adhesive side of said film layer.

16. The reinforced closure anchor of claim 15, wherein said release liner includes a first member and a second member, each of the first member and second member including a first portion mounted on said adhesive side of said film layer and a second portion folded relative to said first portion to form a gripping tab;

wherein one of said first and second members overlaps the other of said first and second members, and one of said first and second members is releasable from said adhesive side of said film layer without tampering with the other of said members.

17. A reinforced closure anchor comprising:

a film layer having an adhesive side, an opposite non-adhesive side, and an outer edge; and an anchor member layer disposed adjacent said film layer, said anchor member layer having a reinforcing structure, a first side, and an opposite second side, said anchor member second side being adhered to said film layer adhesive side;

said anchor member being disposed within the outer edge of said film layer.

18. The reinforced closure anchor of claim 17, wherein said anchor member first side includes an adhesive thereon.

19. The reinforced closure anchor of claim 17, wherein said anchor member first side is free of adhesive.

20. The reinforced closure anchor of claim 17, wherein said anchor member is smaller in surface area than said film layer.

* * * * *